(12) United States Patent
Keshavarz-Shokri et al.

(10) Patent No.: US 8,846,718 B2
(45) Date of Patent: *Sep. 30, 2014

(54) SOLID FORMS OF 3-(6-(1-(2,2-DIFLUOROBENZO[D][1,3]DIOXO1-5-YL)CYCLOPROPANECARBOXAMIDO)-3-METHYLPYRIDIN-2-YL) BENZOIC ACID

(71) Applicant: Vertex Pharmaceuticals Incorporated, Boston, MA (US)

(72) Inventors: Ali Keshavarz-Shokri, San Diego, CA (US); Beili Zhang, San Diego, CA (US); Mariusz Krawiec, Marlborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,223

(22) Filed: Jul. 2, 2013

(65) Prior Publication Data

US 2014/0011846 A1    Jan. 9, 2014

Related U.S. Application Data

(62) Division of application No. 12/327,902, filed on Dec. 4, 2008, now Pat. No. 8,507,534.

(60) Provisional application No. 61/012,162, filed on Dec. 7, 2007.

(51) Int. Cl.
    *A61K 31/443* (2006.01)
    *C07D 405/12* (2006.01)

(52) U.S. Cl.
    CPC .................................. *C07D 405/12* (2013.01)
    USPC ........................................................ 514/338

(58) Field of Classification Search
    USPC ........................................................ 514/338
    See application file for complete search history.

(56) References Cited

U.S. PATENT DOCUMENTS

| | | |
|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida Ruah et al. |
| 8,324,207 B2 | 12/2012 | Hadida-Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor et al. |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel et al. |
| 8,461,352 B2 | 6/2013 | Ambhaikar et al. |
| 2005/0059687 A1 | 3/2005 | Makings |
| 2005/0113423 A1 | 5/2005 | VanGoor et al. |
| 2006/0052358 A1 | 3/2006 | Ruah et al. |
| 2007/0105833 A1 | 5/2007 | Ruah et al. |
| 2008/0071095 A1 | 3/2008 | Hadida-Ruah et al. |
| 2008/0306062 A1 | 12/2008 | Hadida-Ruah et al. |
| 2009/0105272 A1 | 4/2009 | Grootenhuis |
| 2009/0143381 A1 | 6/2009 | Hadida-Ruah et al. |
| 2009/0170905 A1 | 7/2009 | Keshavarz-Shokri et al. |
| 2009/0176839 A1 | 7/2009 | Keshavarz-Shokri et al. |
| 2009/0246820 A1 | 10/2009 | Singh et al. |
| 2009/0253736 A1 | 10/2009 | Hadida-Ruah et al. |
| 2010/0036130 A1 | 2/2010 | Siesel et al. |
| 2010/0074949 A1 | 3/2010 | Rowe et al. |
| 2010/0087490 A1 | 4/2010 | Young et al. |
| 2010/0113508 A1 | 5/2010 | Binch et al. |
| 2010/0125090 A1 | 5/2010 | Hadida-Ruah et al. |
| 2010/0144798 A1 | 6/2010 | VanGoor et al. |
| 2010/0249113 A1 | 9/2010 | Hadida Ruah et al. |
| 2010/0249180 A1 | 9/2010 | Gallardo-Godoy et al. |
| 2010/0256184 A1 | 10/2010 | Rowe et al. |
| 2010/0267768 A1 | 10/2010 | DeMattei et al. |

(Continued)

*Primary Examiner* — Patricia L Morris

(74) *Attorney, Agent, or Firm* — Finnegan, Henderson, Farabow, Garrett & Dunner, LLP

(57) ABSTRACT

The present invention relates to a substantially crystalline and free solid state form of 3-(6-(1-(2,2-difluorobenzo[d][1,3]dioxol-5-yl)cyclopropanecarboxamido)-3-methylpyridin-2-yl)benzoic acid (Form I), pharmaceutical compositions thereof, and methods of treatment therewith.

23 Claims, 11 Drawing Sheets

(56) References Cited

U.S. PATENT DOCUMENTS

| | | |
|---|---|---|
| 2010/0331344 A1 | 12/2010 | Hadida-Ruah et al. |
| 2011/0008259 A1 | 1/2011 | Binch et al. |
| 2011/0060024 A1 | 3/2011 | Hadida Ruah et al. |
| 2011/0064811 A1 | 3/2011 | Hurter et al. |
| 2011/0071206 A1 | 3/2011 | Ruah et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Goor et al. |
| 2011/0263654 A1 | 10/2011 | Keshavarz-Shokri et al. |
| 2011/0288122 A1 | 11/2011 | Van Goor et al. |
| 2011/0306637 A1 | 12/2011 | Hadida-Ruah et al. |
| 2012/0010257 A1 | 1/2012 | Hadida Ruah et al. |
| 2012/0015999 A1 | 1/2012 | Alargova et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0190856 A1 | 7/2012 | Siesel et al. |
| 2012/0208841 A1 | 8/2012 | Binch et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0270869 A1 | 10/2012 | Hadida Ruah et al. |
| 2012/0277268 A1 | 11/2012 | Keshavarz-Shokri et al. |
| 2012/0309758 A1 | 12/2012 | Sheth et al. |
| 2013/0011923 A1 | 1/2013 | Ruah et al. |
| 2013/0012536 A1 | 1/2013 | Hadida Ruah et al. |
| 2013/0018071 A1 | 1/2013 | Arekar et al. |
| 2013/0023538 A1 | 1/2013 | Hadida Ruah et al. |
| 2013/0035327 A1 | 2/2013 | Hadida-Ruah et al. |
| 2013/0040986 A1 | 2/2013 | Binch et al. |
| 2013/0072522 A1 | 3/2013 | DeMattei et al. |
| 2013/0072687 A1 | 3/2013 | Ambhaikar et al. |
| 2013/0079367 A1 | 3/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0109717 A1 | 5/2013 | DeMattei et al. |
| 2013/0116238 A1 | 5/2013 | Looker et al. |
| 2013/0131107 A1 | 5/2013 | Van Goor et al. |
| 2013/0137722 A1 | 5/2013 | Zhang et al. |
| 2013/0143918 A1 | 6/2013 | Keshavarz-Shokri et al. |
| 2013/0143919 A1 | 6/2013 | Van Goor et al. |
| 2013/0158071 A1 | 6/2013 | Van Goor et al. |
| 2013/0296306 A1 | 11/2013 | Hadida-Ruah et al. |
| 2013/0296364 A1 | 11/2013 | Hadida-Ruah et al. |
| 2013/0296379 A1 | 11/2013 | Keshavarz-Shokri et al. |
| 2013/0303484 A1 | 11/2013 | Grootenhuis et al. |
| 2013/0303570 A1 | 11/2013 | Binch et al. |
| 2013/0317020 A1 | 11/2013 | Ruah et al. |
| 2013/0324743 A1 | 12/2013 | Belmont et al. |
| 2013/0331567 A1 | 12/2013 | Hadida-Ruah et al. |
| 2014/0011846 A1 | 1/2014 | Keshavarz-Shokri et al. |
| 2014/0023706 A1 | 1/2014 | Verwijs et al. |
| 2014/0024672 A1 | 1/2014 | Hadida-Ruah et al. |
| 2014/0051724 A1 | 2/2014 | Hadida-Ruah et al. |
| 2014/0057906 A1 | 2/2014 | Hadida-Ruah et al. |
| 2014/0072995 A1 | 3/2014 | Hadida-Ruah et al. |
| 2014/0073653 A1 | 3/2014 | Binch et al. |

SOLID FORMS OF 3-(6-(1-(2,2-DIFLUOROBENZO[D][1,3]DIOXOL-5-YL)CYCLOPROPANECARBOXAMIDO)-3-METHYLPYRIDIN-2-YL) BENZOIC ACID

CROSS REFERENCE TO RELATED APPLICATIONS

This application is a divisional of U.S. patent application Ser. No. 12/327,902, filed Dec. 4, 2008, which claims the benefit under 35 U.S.C. §119 to U.S. provisional patent application Ser. No. 61/012,162, filed Dec. 7, 2007, the entire contents of both applications are incorporated herein by reference.

TECHNICAL FIELD OF THE INVENTION

The present invention relates to solid state forms, for example, crystalline forms, of 3-(6-(1-(2,2-difluorobenzo[d][1,3]dioxol-5-yl)cyclopropanecarboxamido)-3-methylpyridin-2-yl)benzoic acid, pharmaceutical compositions thereof, and methods therewith.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl– channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

3-(6-(1-(2,2-Difluorobenzo[d][1,3]dioxol-5-yl)cyclopropanecarboxamido)-3-methylpyridin-2-yl)benzoic acid in salt form is disclosed in International PCT Publication WO 2007056341 (said publication being incorporated herein by reference in its entirety) as a modulator of CFTR activity and thus useful in treating CFTR-mediated diseases such as cystic fibrosis. However, there is a need for stable solid forms of said compound that can be used readily in pharmaceutical compositions suitable for use as therapeutics.

SUMMARY OF THE INVENTION

The present invention relates to solid forms of 3-(6-(1-(2,2-difluorobenzo[d][1,3]dioxol-5-yl)cyclopropanecarboxamido)-3-methylpyridin-2-yl)benzoic acid (hereinafter "Compound 1") which has the structure below:

Compound 1

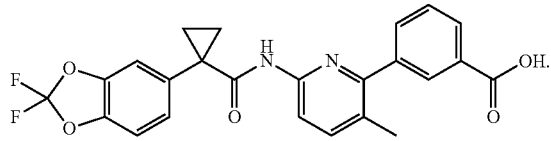

Compound 1 and pharmaceutically acceptable compositions thereof are useful for treating or lessening the severity of cystic fibrosis. In one aspect, Compound 1 is in a substantially crystalline and salt free form referred to as Form I as described and characterized herein.

Processes described herein can be used to prepare the compositions of this invention comprising Form I. The amounts and the features of the components used in the processes would be as described herein.

DETAILED DESCRIPTION OF THE INVENTION

Definitions

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "modulating" as used herein means increasing or decreasing, e.g. activity, by a measurable amount.

In one aspect, the invention features a form of 3-(6-(1-(2,2-difluorobenzo[d][1,3]dioxol-5-yl)cyclopropanecarboxamido)-3-methylpyridin-2-yl)benzoic acid characterized as Form I.

In another embodiment, Form I is characterized by one or more peaks at 15.2 to 15.6 degrees, 16.1 to 16.5 degrees, and 14.3 to 14.7 degrees in an X-ray powder diffraction obtained using Cu K alpha radiation.

In another embodiment, Form I is characterized by one or more peaks at 15.4, 16.3, and 14.5 degrees.

In another embodiment, Form I is further characterized by a peak at 14.6 to 15.0 degrees.

In another embodiment, Form I is further characterized by a peak at 14.8 degrees.

In another embodiment, Form I is further characterized by a peak at 17.6 to 18.0 degrees.

In another embodiment, Form I is further characterized by a peak at 17.8 degrees.

In another embodiment, Form I is further characterized by a peak at 16.4 to 16.8 degrees.

In another embodiment, Form I is further characterized by a peak at 16.4 to 16.8 degrees.

In another embodiment, Form I is further characterized by a peak at 16.6 degrees.

In another embodiment, Form I is further characterized by a peak at 7.6 to 8.0 degrees.

In another embodiment, Form I is further characterized by a peak at 7.8 degrees.

In another embodiment, Form I is further characterized by a peak at 25.8 to 26.2 degrees.

In another embodiment, Form I is further characterized by a peak at 26.0 degrees.

In another embodiment, Form I is further characterized by a peak at 21.4 to 21.8 degrees.

In another embodiment, Form I is further characterized by a peak at 21.6 degrees.

In another embodiment, Form I is further characterized by a peak at 23.1 to 23.5 degrees.

In another embodiment, Form I is further characterized by a peak at 23.3 degrees.

Figure 1:
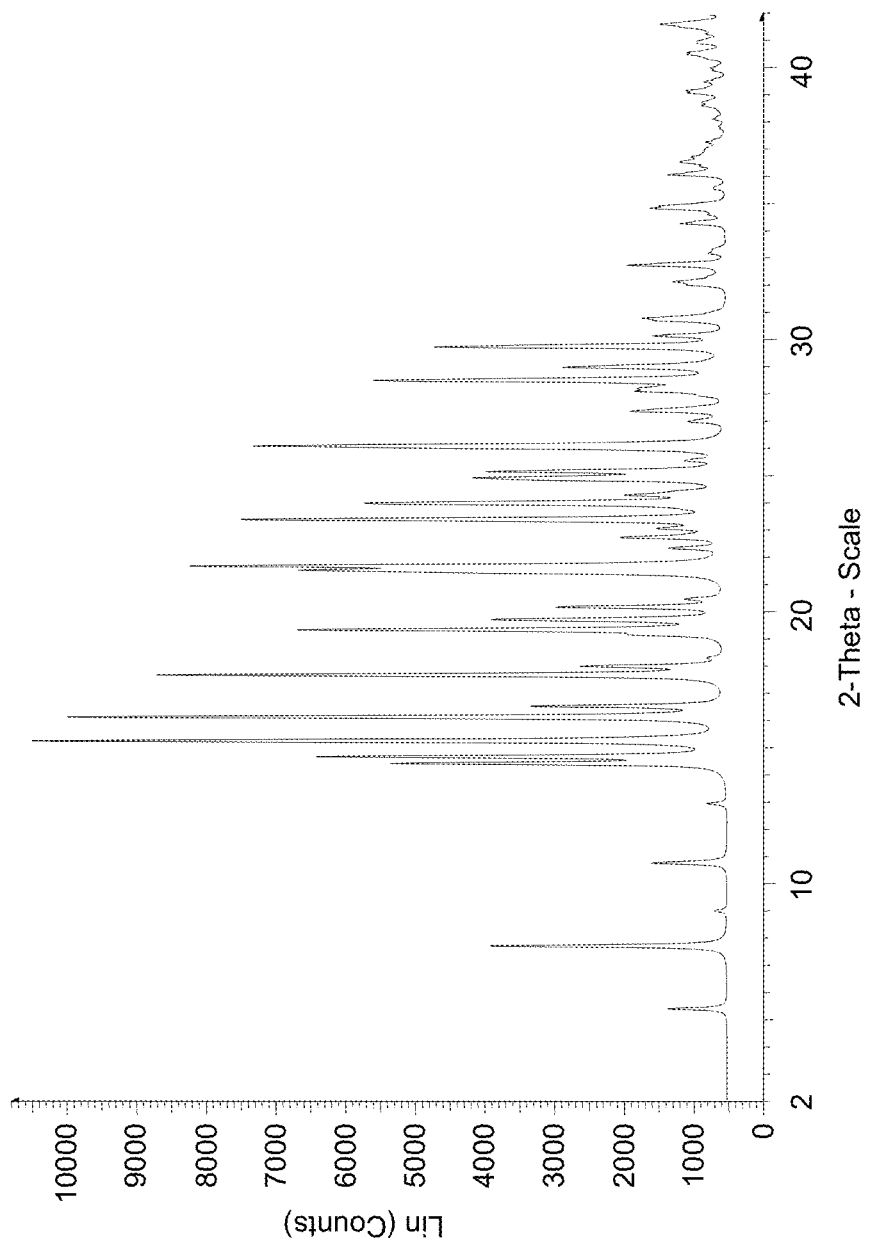
FIG. 1 is an X-ray diffraction pattern calculated from a single crystal structure of Compound 1 in Form I.

In some embodiments, Form I is characterized by a diffraction pattern substantially similar to that of FIG. 1.

Figure 2:
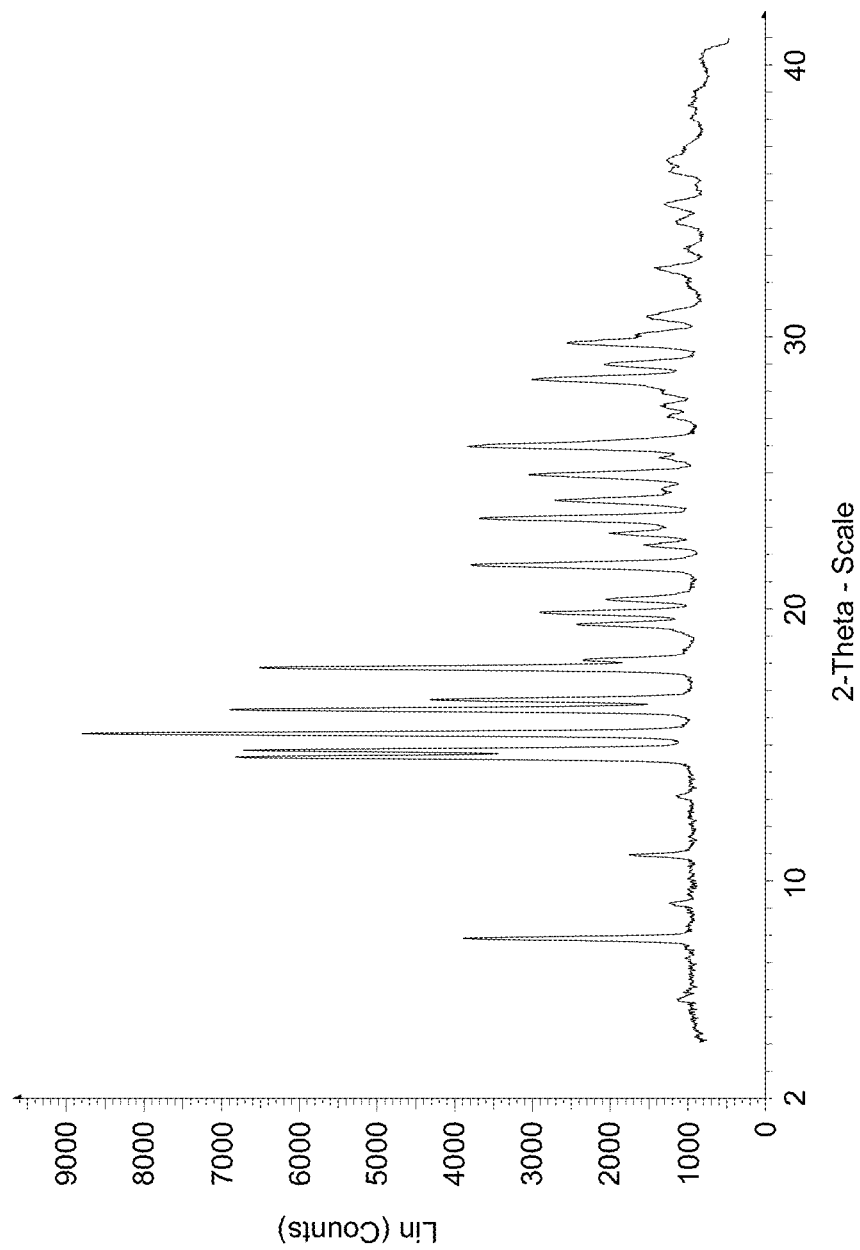
FIG. 2 is an actual X-ray powder diffraction pattern of Compound 1 in Form I.

In some embodiments, Form I is characterized by a diffraction pattern substantially similar to that of FIG. 2.

In some embodiments, the particle size distribution of D90 is about 82 μm or less for Form I.

In some embodiments, the particle size distribution of D50 is about 30 μm or less for Form I.

In one aspect, the invention features a pharmaceutical composition comprising Form I and a pharmaceutically acceptable carrier.

In one aspect, the present invention features a method of treating a CFTR mediated disease in a human comprising administering to the human an effective amount of Form I.

In some embodiments, the method comprises administering an additional therapeutic agent.

In some embodiements, the disease is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease.

In one embodiment, the present invention provides a method of treating cystic fibrosis in a human, comprising administering to said human an effective amount of Form I.

In one aspect, the present invention features a kit comprising Form I and instructions for use thereof.

In one aspect, the present invention features a process of preparing Form I comprising dispersing or dissolving the HCl salt of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time.

In one embodiment, the present invention features a process of preparing Form I comprising dispersing the HCl salt of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time.

In some embodiments, the appropriate solvent is water or a alcohol/water mixture.

In some embodiments, the appropriate solvent is water or 50% methanol/water mixture.

In some embodiments, the appropriate solvent is water.

In some embodiments, the appropriate solvent is a mixture comprising 50% methanol and 50% water.

In some embodiments, the effective amount of time is about 2 to about a day. In some embodiments, the effective amount of time is about 2 to about 18 hours. In some embodiments, the effective amount of time is about 2 to about 12 hours. In some embodiments, the effective amount of time is about 2 to about 6 hours.

In one aspect, the invention features a crystal form of 3-(6-(1-(2,2-difluorobenzo[d][1,3]dioxol-5-yl)cyclopropanecarboxamido)-3-methylpyridin-2-yl)benzoic acid having a monoclinic crystal system, a $P2_1/n$ space group, and the following unit cell dimensions: a=4.9626 (7) Å, b=12.2994 (18) Å, c=33.075 (4) Å, α=90°, β=93.938 (9)°, and γ=90°.

Methods of Preparing Form I

In one embodiment, Form I is prepared from dispersing or dissolving a salt form, such as HCL, of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time. In another embodiment, Form I is prepared from dispersing a salt form, such as HCL, of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time. In another embodiment, Form I is formed directly from 3-(6-(1-(2,2-difluorobenzo[d][1,3]dioxol-5-yl)cyclopropanecarboxamido)-3-methylpyridin-2-yl)-t-butylbenzoate and an appropriate acid, such as formic acid. In one embodiment, the HCl salt form of 3-(6-(1-(2,2-difluorobenzo[d][1,3]dioxol-5-yl)cyclopropanecarboxamido)-3-methylpyridin-2-yl)benzoic acid is the starting point and in one embodiment can be prepared by coupling an acid chloride moiety with an amine moiety according to Schemes 1-3.

Scheme 1. Synthesis of the acid chloride moiety.

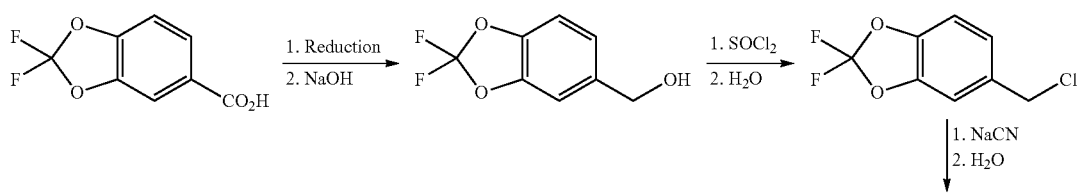

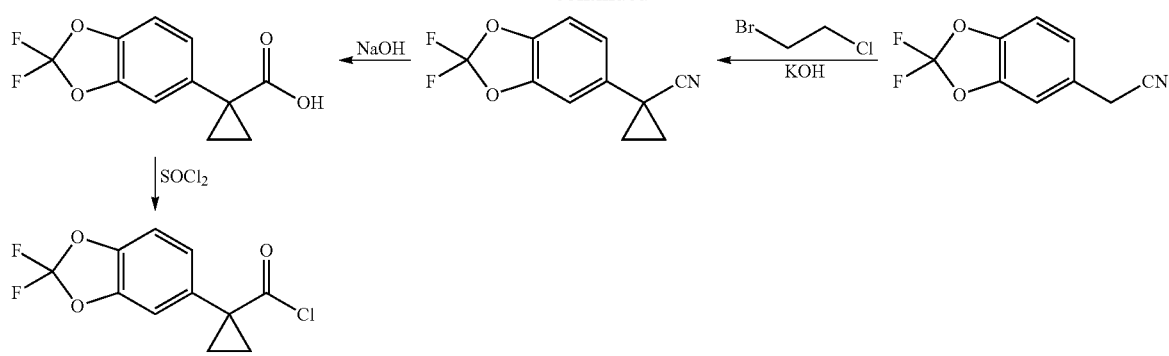
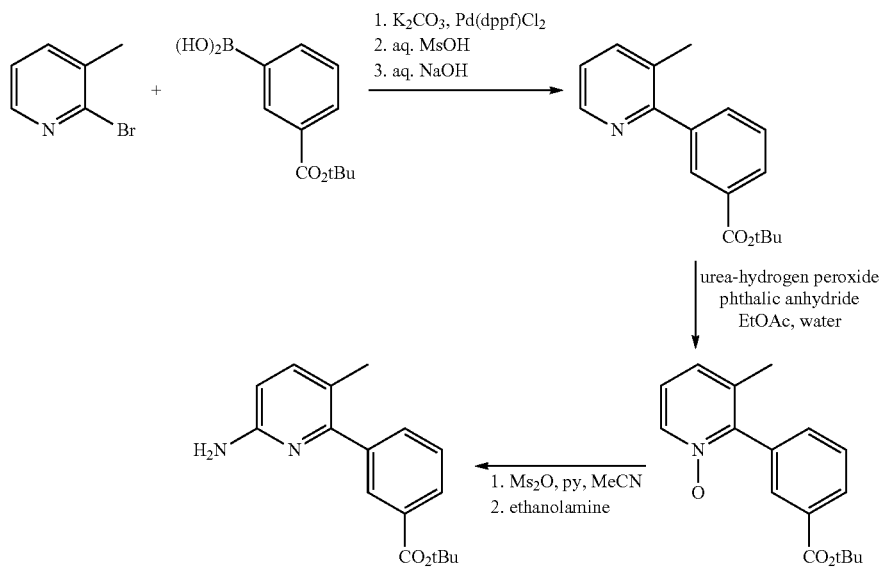
Scheme 2. Synthesis of the amine moiety.
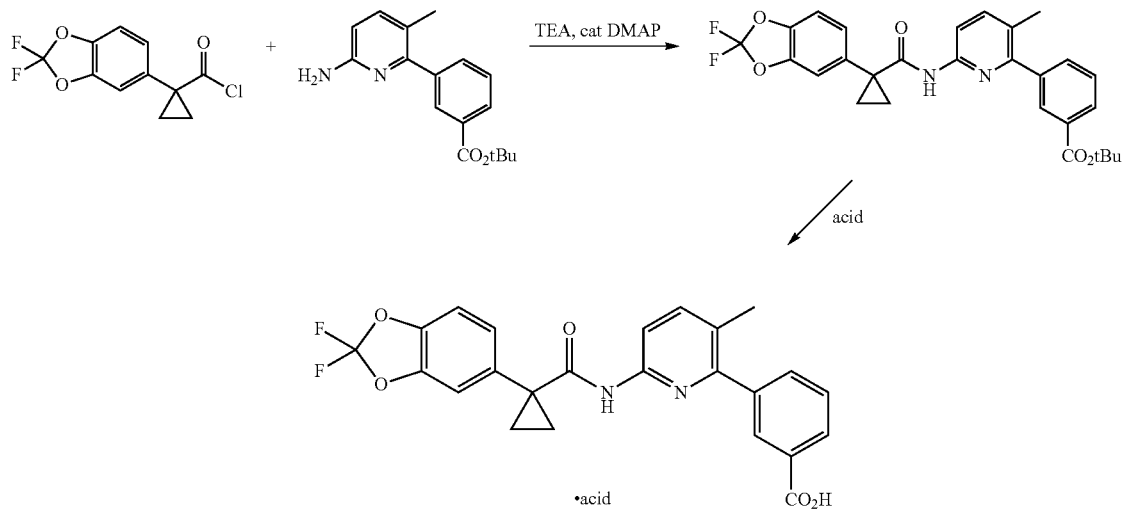
Scheme 3. Formation of an acid salt of 3-(6-(1-(2,2-difluorobenzo[d][1,3]dioxol-5-yl) cyclopropanecarboxamido)-3-methylpyridin-2-yl)benzoic acid.

Using the HCl, for example, salt form of 3-(6-(1-(2,2-difluorobenzo[d][1,3]dioxol-5-yl)cyclopropanecarboxamido)-3-methylpyridin-2-yl)benzoic acid as a starting point, Form I can be formed in high yields by dispersing or dissolving the HCl salt form of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time. Other salt forms of 3-(6-(1-(2,2-difluorobenzo[d][1,3]dioxol-5-yl)cyclopropanecarboxamido)-3-methylpyridin-2-yl)benzoic acid may be used such as, for example, other mineral or organic acid forms. The other salt forms result from hydrolysis of the t-butyl ester with the corresponding acid. Other acids/salt forms include nitric, sulfuric, phosphoric, boric, acetic, benzoic, malonic, and the like. The salt form of 3-(6-(1-(2,2-difluorobenzo[d][1,3]dioxol-5-yl)cyclopropanecarboxamido)-3-methylpyridin-2-yl)benzoic acid may or may not be soluble depending upon the solvent used, but lack of solubility does not hinder formation of Form I. For example, in one embodiment, the appropriate solvent may be water or an alcohol/water mixture such as 50% methanol/water mixture, even though the HCl salt form of 3-(6-(1-(2,2-difluorobenzo[d][1,3]dioxol-5-yl)cyclopropanecarboxamido)-3-methylpyridin-2-yl)benzoic acid is only sparingly soluble in water. In one embodiment, the appropriate solvent is water.

The effective amount of time for formation of Form I from the salt form of 3-(6-(1-(2,2-difluorobenzo[d][1,3]dioxol-5-yl)cyclopropanecarboxamido)-3-methylpyridin-2-yl)benzoic acid can be any time between 2 to 24 hours or greater. Generally, greater than 24 hours is not needed to obtain high yields (~98%), but certain solvents may require greater amounts of time. It is also recognized that the amount of time needed is inversely proportional to the temperature. That is, the higher the temperature the less time needed to affect dissociation of acid to form Form I. When the solvent is water, stirring the dispersion for approximately 24 hours at room temperature gives Form I in an approximately 98% yield. If a solution of the salt form of 3-(6-(1-(2,2-difluorobenzo[d][1,3]dioxol-5-yl)cyclopropanecarboxamido)-3-methylpyridin-2-yl)benzoic acid is desired for process purposes, an elevated temperature may be used. After stirring the solution for an effective amount of time at the elevated temperature, recrystallization upon cooling yields substantially pure forms of Form I. In one embodiment, substantially pure refers to greater than about 90% purity. In another embodiment, substantially pure refers to greater than about 95% purity. In another embodiment, substantially pure refers to greater than about 98% purity. In another embodiment, substantially pure refers to greater than about 99% purity. The temperature selected depends in part on the solvent used and is well within the capabilities of someone of ordinary skill in the art to determine. In one embodiment, the temperature is between room temperature and about 80° C. In another embodiment, the temperature is between room temperature and about 40° C. In another embodiment, the temperature is between about 40° C. and about 60° C. In another embodiment, the temperature is between about 60° C. and about 80° C.

In some embodiments, Form I may be further purified by recrystallization from an organic solvent. Examples of organic solvents include, but are not limited to, toluene, cumene, anisole, 1-butanol, isopropylacetate, butyl acetate, isobutyl acetate, methyl t-butyl ether, methyl isobutyl ketone, or 1-propanol/water (at various ratios). Temperature may be used as described above. For example, in one embodiment, Form I is dissolved in 1-butanol at 75° C. until it is completely dissolved. Cooling down the solution to 10° C. at a rate of 0.2° C./min yields crystals of Form I which may be isolated by filtration.

Uses, Formulation and Administration
Pharmaceutically Acceptable Compositions

In another aspect of the present invention, pharmaceutically acceptable compositions are provided, wherein these compositions comprise Form I as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a solid state form of Form I described herein to a subject, preferably a mammal, in need thereof.

A "CFTR-mediated disease" as used herein is a disease selected from cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

In certain embodiments, the present invention provides a method of treating a CFTR-mediated disease in a human comprising the step of administering to said human an effective amount of a composition comprising Form I described herein.

According to an alternative preferred embodiment, the present invention provides a method of treating cystic fibrosis in a human comprising the step of administering to said human a composition comprising Form I described herein.

According to the invention an "effective amount" of Form I or a pharmaceutically acceptable composition thereof is that amount effective for treating or lessening the severity of any of the diseases recited above.

Form I or a pharmaceutically acceptable composition thereof may be administered using any amount and any route of administration effective for treating or lessening the severity of one or more of the diseases reicted above.

In certain embodiments, Form I described herein or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl$^-$ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, $\Delta$F508.

In one embodiment, Form I described herein or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Form I described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In certain embodiments, the dosage amount of Form I in the dosage unit form is from 100 mg to 1,000 mg. In another embodiment, the dosage amount of Form I is from 200 mg to 900 mg. In another embodiment, the dosage amount of Form I is from 300 mg to 800 mg. In another embodiment, the dosage amount of Form I is from 400 mg to 700 mg. In another embodiment, the dosage amount of Form I is from 500 mg to 600 mg.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

It will also be appreciated that Form I described herein or a pharmaceutically acceptable composition thereof can be employed in combination therapies, that is, Form I can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, aminone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound disclosed in WO 2004028480, WO 2004110352, WO 2005094374, WO 2005120497, or WO 2006101740.

In another embodiment, the additiona agent is a benzo[c]quinolizinium derivative that exhibits CFTR modulation activity or a benzopyran derivative that exhibits CFTR modulation activity.

In another embodiment, the addditional agent is a compound disclosed in US7202262, US6992096, US20060148864, US20060148863, US20060035943, US20050164973, WO2006110483, WO2006044456, WO2006044682, WO2006044505, WO2006044503, WO2006044502, or WO2004091502.

In another embodiment, the additional agent is a compound disclosed in WO2004080972, WO2004111014, WO2005035514, WO2005049018, WO2006002421, WO2006099256, WO2006127588, or WO2007044560.

In another embodiment, the an additional agent selected from compounds disclosed in U.S. patent application Ser. No. 11/165,818, published as U.S. Published Patent Application No. 2006/0074075, filed Jun. 24, 2005, and hereby incorporated by reference in its entirety. In another embodiment, the additional agent is N-(5-hydroxy-2,4-ditert-butyl-phenyl)-4-oxo-1H-quinoline-3-carboxamide. These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Form I described herein or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising Form I described herein or a pharmaceutically acceptable composition thereof, and in classes and subclasses herein, and a carrier suitable for coating said implantable device. In still another aspect, the present invention includes an implantable device coated with a composition comprising Form I described herein or a pharmaceutically acceptable composition thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

In order that the invention described herein may be more fully understood, the following examples are set forth. It should be understood that these examples are for illustrative purposes only and are not to be construed as limiting this invention in any manner.

EXAMPLES

Methods & Materials

Differential Scanning Calorimetry (DSC)

The Differential scanning calorimetry (DSC) data of Form I were collected using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were scanned from 25° C. to 350° C. at a heating rate of 1.0° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

XRPD (X-ray Powder Diffraction)

The X-Ray diffraction (XRD) data of Form 1 were collected on a Bruker D8 DISCOVER powder diffractometer with HI-STAR 2-dimensional detector and a flat graphite monochromator. Cu sealed tube with Kα radiation was used at 40 kV, 35 mA. The samples were placed on zero-background silicon wafers at 25° C. For each sample, two data frames were collected at 120 seconds each at 2 different $\theta_2$ angles: 8° and 26°. The data were integrated with GADDS software and merged with DIFFRACT$^{plus}$EVA software. Uncertainties for the reported peak positions are ±0.2 degrees.

Vitride® (sodium bis(2-methoxyethoxy)aluminum hydride [or $NaAlH_2(OCH_2CH_2OCH_3)_2$], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of 3-(6-(1-(2,2-difluorobenzo[d][1,3]dioxol-5-yl)cyclopropanecarboxamido)-3-methylpyridin-2-yl)benzoic acid.HCl Acid Chloride Moiety Synthesis of (2,2-difluoro-1,3-benzodioxol-5-yl)-methanol

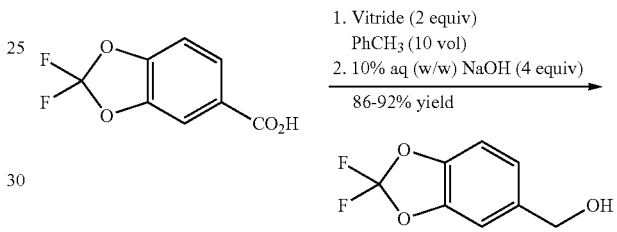

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at 40° C. The organic phase is cooled to 20° C. then washed with water (2×1.5 vol), dried ($Na_2SO_4$), filtered, and concentrated to afford crude (2,2-difluoro-1,3-benzodioxol-5-yl)-methanol that is used directly in the next step.

Synthesis of 5-chloromethyl-2,2-difluoro-1,3-benzodioxole

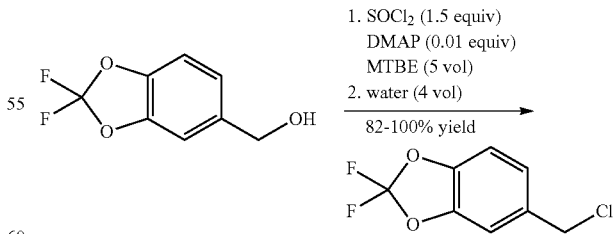

(2,2-difluoro-1,3-benzodioxol-5-yl)-methanol (1.0 eq) is dissolved in MTBE (5 vol). A catalytic amount of DMAP (1 mol %) is added and $SOCl_2$ (1.2 eq) is added via addition funnel. The $SOCl_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na$_2$SO$_4$), filtered, and concentrated to afford crude 5-chloromethyl-2,2-difluoro-1,3-benzodioxole that is used directly in the next step.

Synthesis of
(2,2-difluoro-1,3-benzodioxol-5-yl)-acetonitrile

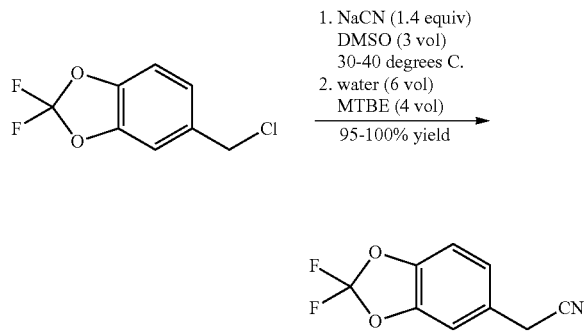

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na$_2$SO$_4$), filtered, and concentrated to afford crude (2,2-difluoro-1,3-benzodioxol-5-yl)-acetonitrile (95%) that is used directly in the next step.

Synthesis of (2,2-difluoro-1,3-benzodioxol-5-yl)-cyclopropanecarbonitrile

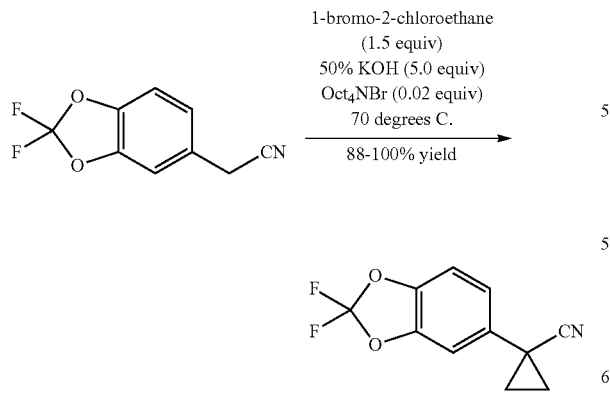

A mixture of (2,2-difluoro-1,3-benzodioxol-5-yl)-acetonitrile (1.0 eq), 50 wt % aqueous KOH (5.0 eq) 1-bromo-2-chloroethane (1.5 eq), and Oct$_4$NBr (0.02 eq) is heated at 70° C. for 1 h. The reaction mixture is cooled then worked up with MTBE and water. The organic phase is washed with water and brine then the solvent is removed to afford (2,2-difluoro-1,3-benzodioxol-5-yl)-cyclopropanecarbonitrile.

Synthesis of 1-(2,2-difluoro-1,3-benzodioxol-5-yl)-cyclopropanecarboxylic acid

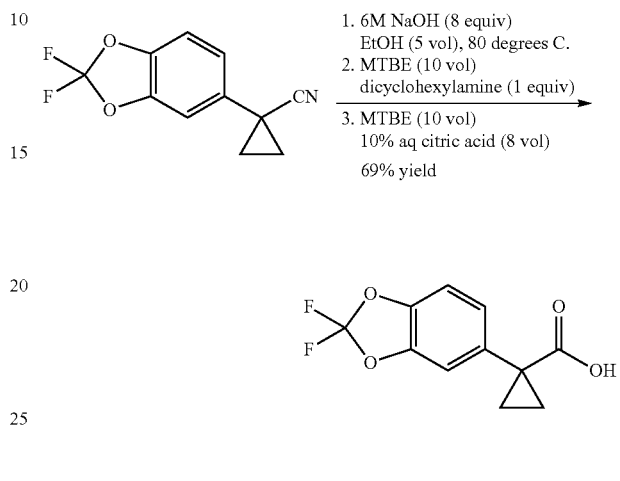

(2,2-difluoro-1,3-benzodioxol-5-yl)-cyclopropanecarbonitrile is hydrolyzed using 6 M NaOH (8 equiv) in ethanol (5 vol) at 80° C. overnight. The mixture is cooled to room temperature and ethanol is evaporated under vacuum. The residue is taken into water and MTBE, 1 M HCl was added and the layers are separated. The MTBE layer was then treated with dicyclohexylamine (0.97 equiv). The slurry is cooled to 0° C., filtered and washed with heptane to give the corresponding DCHA salt. The salt is taken into MTBE and 10% citric acid and stirred until all solids dissolve. The layers are separated and the MTBE layer was washed with water and brine. Solvent swap to heptane followed by filtration gives 1-(2,2-difluoro-1,3-benzodioxol-5-yl)-cyclopropanecarboxylic acid after drying in a vacuum oven at 50° C. overnight.

Synthesis of 1-(2,2-difluoro-1,3-benzodioxol-5-yl)-cyclopropanecarbonyl chloride

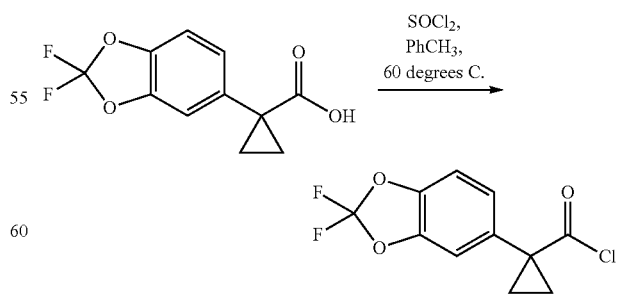

1-(2,2-difluoro-1,3-benzodioxol-5-yl)-cyclopropanecarboxylic acid (1.2 eq) is slurried in toluene (2.5 vol) and the mixture heated to 60° C. SOCl$_2$ (1.4 eq) is added via addition funnel. The toluene and SOCl₂ are distilled from the reaction mixture after 30 minutes. Additional toluene (2.5 vol) is added and distilled again.

Amine Moiety

Synthesis of
tert-butyl-3-(3-methylpyridin-2-yl)benzoate

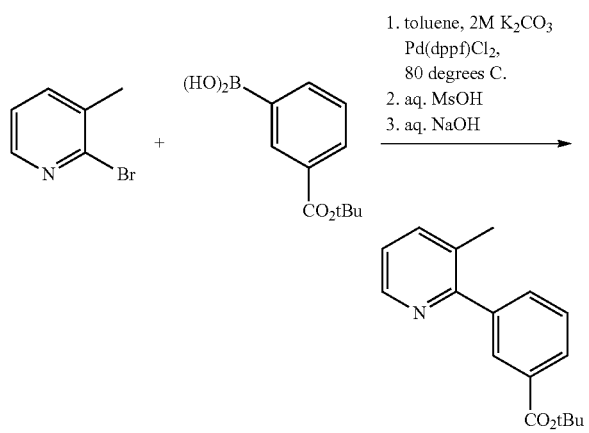

2-Bromo-3-methylpyridine (1.0 eq) is dissolved in toluene (12 vol). K₂CO₃ (4.8 eq) is added followed by water (3.5 vol) and the mixture heated to 65° C. under a stream of N₂ for 1 hour. 3-(t-Butoxycarbonyl)phenylboronic acid (1.05 eq) and Pd(dppf)Cl₂.CH₂Cl₂ (0.015 eq) are then added and the mixture is heated to 80° C. After 2 hours, the heat is turned off, water is added (3.5 vol) and the layers are allowed to separate. The organic phase is then washed with water (3.5 vol) and extracted with 10% aqueous methanesulfonic acid (2 eq MsOH, 7.7 vol). The aqueous phase is made basic with 50% aqueous NaOH (2 eq) and extracted with EtOAc (8 vol). The organic layer is concentrated to afford crude tert-butyl-3-(3-methylpyridin-2-yl)benzoate (82%) that is used directly in the next step.

Synthesis of 2-(3-(tert-butoxycarbonyl)phenyl)-3-methylpyridine-1-oxide

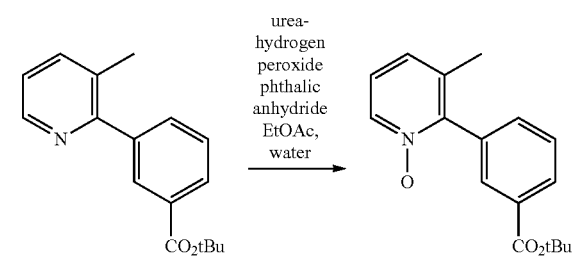

tert-Butyl-3-(3-methylpyridin-2-yl)benzoate (1.0 eq) is dissolved in EtOAc (6 vol). Water (0.3 vol) is added followed by urea-hydrogen peroxide (3 eq). The phthalic anhydride (3 eq) is added portion-wise as a solid to maintain the temperature in the reactor below 45° C. After completion of phthalic anhydride addition, the mixture is heated to 45° C. After stirring for an additional 4 hours, the heat is turned off 10% w/w aqueous Na₂SO₃ (1.5 eq) is added via addition funnel. After completion of Na₂SO₃ addition, the mixture is stirred for an additional 30 minutes and the layers separated. The organic layer is stirred and 10% w/w aq. Na₂CO₃ (2 eq) is added. After stirring for 30 minutes, the layers are allowed to separate. The organic phase is washed 13% w/v aq NaCl. The organic phase is then filtered and concentrated to afford crude 2-(3-(tert-butoxycarbonyl)phenyl)-3-methylpyridine-1-oxide (95%) that is used directly in the next step.

Synthesis of tert-butyl-3-(6-amino-3-methylpyridin-2-yl)benzoate

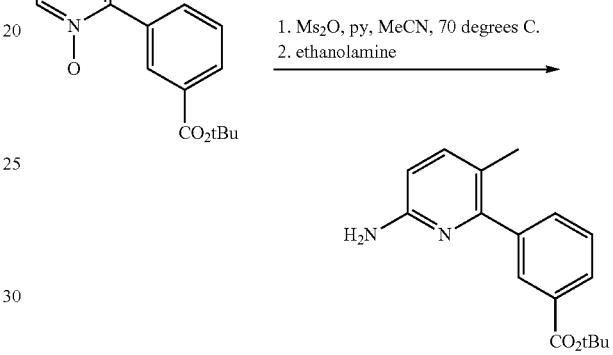

A solution of 2-(3-(tert-butoxycarbonyl)phenyl)-3-methylpyridine-1-oxide (1 eq) and pyridine (4 eq) in MeCN (8 vol) is heated to 70° C. A solution of methanesulfonic anhydride (1.5 eq) in MeCN (2 vol) is added over 50 min via addition funnel maintaining the temperature at less than 75° C. The mixture is stirred for an additional 0.5 hours after complete addition. The mixture is then allowed to cool to ambient. Ethanolamine (10 eq) is added via addition funnel. After stirring for 2 hours, water (6 vol) is added and the mixture is cooled to 10° C. After stirring for NLT 3 hours, the solid is collected by filtration and washed with water (3 vol), 2:1 MeCN/water (3 vol), and MeCN (2×1.5 vol). The solid is dried to constant weight (<1% difference) in a vacuum oven at 50° C. with a slight N₂ bleed to afford tert-butyl-3-(6-amino-3-methylpyridin-2-yl)benzoate as a red-yellow solid (53% yield).

Synthesis of 3-(6-(1-(2,2-difluorobenzo[d][1,3]dioxol-5-yl)cyclopropanecarboxamido)-3-methylpyridin-2-yl)-t-butylbenzoate

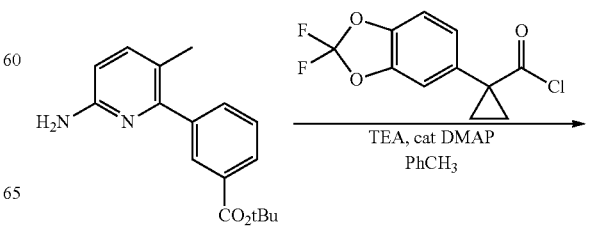

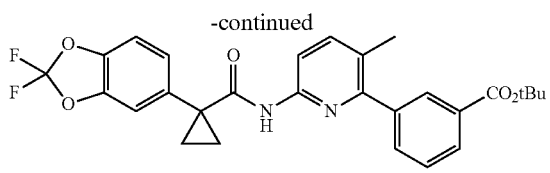

-continued

The crude acid chloride is dissolved in toluene (2.5 vol based on acid chloride) and added via addition funnel to a mixture of tert-butyl-3-(6-amino-3-methylpyridin-2-yl)benzoate (1 eq), dimethylaminopyridine (DMAP, 0.02 eq), and triethylamine (3.0 eq) in toluene (4 vol based on tert-butyl-3-(6-amino-3-methylpyridin-2-yl)benzoate). After 2 hours, water (4 vol based on tert-butyl-3-(6-amino-3-methylpyridin-2-yl)benzoate) is added to the reaction mixture. After stirring for 30 minutes, the layers are separated. The organic phase is then filtered and concentrated to afford a thick oil of 3-(6-(1-(2,2-difluorobenzo[d][1,3]dioxol-5-yl)cyclopropanecarboxamido)-3-methylpyridin-2-yl)-t-butylbenzoate (quantitative crude yield). MeCN (3 vol based on crude product) is added and distilled until crystallization occurs. Water (2 vol based on crude product) is added and the mixture stirred for 2 h. The solid is collected by filtration, washed with 1:1 (by volume) MeCN/water (2×1 vol based on crude product), and partially dried on the filter under vacuum. The solid is dried to constant weight (<1% difference) in a vacuum oven at 60° C. with a slight $N_2$ bleed to afford 3-(6-(1-(2,2-difluorobenzo[d][1,3]dioxol-5-yl)cyclopropanecarboxamido)-3-methylpyridin-2-yl)-t-butylbenzoate as a brown solid.

Synthesis of 3-(6-(1-(2,2-difluorobenzo[d][1,3]dioxol-5-yl)cyclopropanecarboxamido)-3-methylpyridin-2-yl)benzoic acid.HCL salt

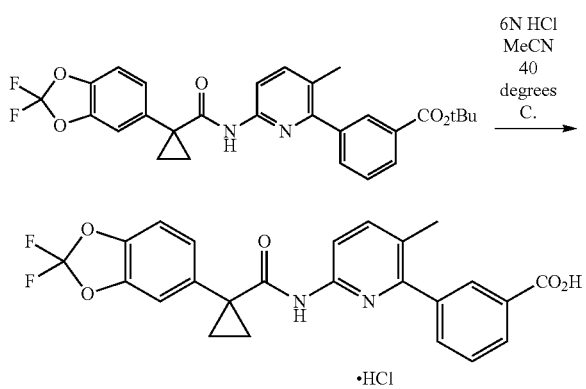

To a slurry of 3-(6-(1-(2,2-difluorobenzo[d][1,3]dioxol-5-yl)cyclopropanecarboxamido)-3-methylpyridin-2-yl)-t-butylbenzoate (1.0 eq) in MeCN (3.0 vol) is added water (0.83 vol) followed by concentrated aqueous HCl (0.83 vol). The mixture is heated to 45±5° C. After stirring for 24 to 48 hours the reaction is complete and the mixture is allowed to cool to ambient. Water (1.33 vol) is added and the mixture stirred. The solid is collected by filtration, washed with water (2×0.3 vol), and partially dried on the filter under vacuum. The solid is dried to constant weight (<1% difference) in a vacuum oven at 60° C. with a slight $N_2$ bleed to afford 3-(6-(1-(2,2-difluorobenzo[d][1,3]dioxol-5-yl)cyclopropanecarboxamido)-3-methylpyridin-2-yl)benzoic acid.HCl as an off-white solid.

Synthesis of 3-(6-(1-(2,2-difluorobenzo[d][1,3]dioxol-5-yl)cyclopropanecarboxamido)-3-methylpyridin-2-yl)benzoic acid (Form I)

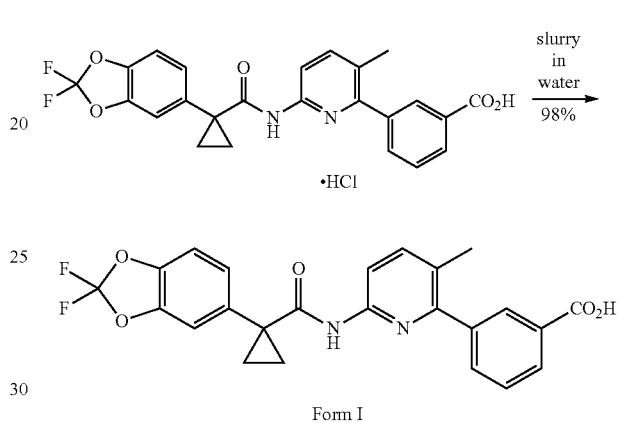

A slurry of 3-(6-(1-(2,2-difluorobenzo[d][1,3]dioxol-5-yl)cyclopropanecarboxamido)-3-methylpyridin-2-yl)benzoic acid.HCl (1 eq) in water (10 vol) is stirred at ambient temperature. A sample is taken after stirring for 24 hours. The sample is filtered and the solid washed with water (2×). The solid sample is submitted for DSC analysis. When DSC analysis indicates complete conversion to Form I, the solid is collected by filtration, washed with water (2×1.0 vol), and partially dried on the filter under vacuum. The solid is dried to constant weight (<1% difference) in a vacuum oven at 60° C. with a slight $N_2$ bleed to afford Form I as an off-white solid (98% yield). $^1$H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H).

Synthesis of 3-(6-(1-(2,2-difluorobenzo[d][1,3]dioxol-5-yl)cyclopropanecarboxamido)-3-methylpyridin-2-yl)benzoic acid (Form I) using water and base

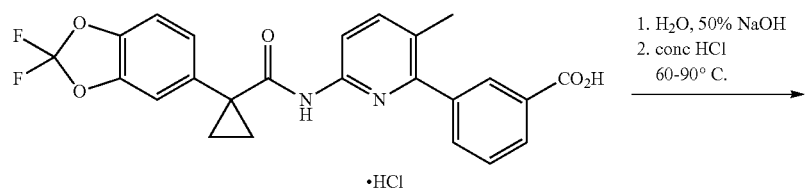

-continued

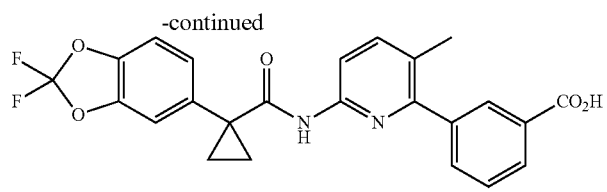

Form I

To a slurry of 3-(6-(1-(2,2-difluorobenzo[d][1,3]dioxol-5-yl)cyclopropanecarboxamido)-3-methylpyridin-2-yl)benzoic acid.HCl (1 eq) in water (10 vol) stirred at ambient temperature is added 50% w/w aq. NaOH (2.5 eq). The mixture is stirred for NLT 15 min or until a homogeneous solution. Concentrated HCl (4 eq) is added to crystallize Form I. The mixture is heated to 60° C. or 90° C. if needed to reduce the level of the t-butylbenzoate ester. The mixture is heated until HPLC analysis indicates NMT 0.8% (AUC) t-butylbenzoate ester. The mixture is then cooled to ambient and the solid is collected by filtration, washed with water (3×3.4 vol), and partially dried on the filter under vacuum. The solid is dried to constant weight (<1% difference) in a vacuum oven at 60° C. with a slight $N_2$ bleed to afford Form I as an off-white solid (97% yield).

Synthesis of 3-(6-(1-(2,2-difluorobenzo[d][1,3]dioxol-5-yl)cyclopropanecarboxamido)-3-methylpyridin-2-yl)benzoic acid (Form I) directly from benzoate

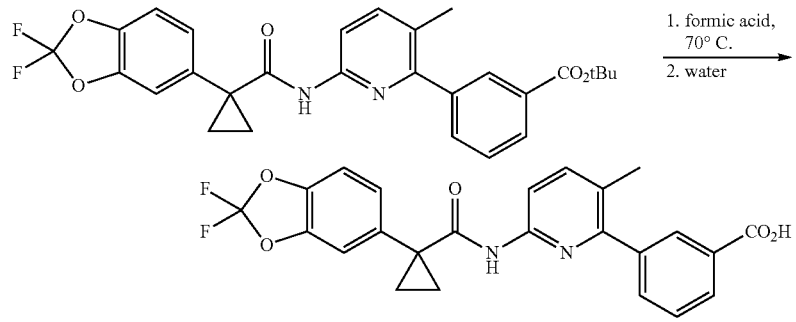

Form I

A solution of 3-(6-(1-(2,2-difluorobenzo[d][1,3]dioxol-5-yl)cyclopropanecarboxamido)-3-methylpyridin-2-yl)-t-butylbenzoate (1.0 eq) in formic acid (3.0 vol) is heated to 70±10° C. The reaction is continued until the reaction is complete (NMT 1.0% AUC 3-(6-(1-(2,2-difluorobenzo[d][1,3]dioxol-5-yl)cyclopropanecarboxamido)-3-methylpyridin-2-yl)-t-butylbenzoate) or heating for NMT 8 h. The mixture is allowed to cool to ambient. The solution is added to water (6 vol) heated at 50° C. and the mixture stirred. The mixture is then heated to 70±10° C. until the level of 3-(6-(1-(2,2-difluorobenzo[d][1,3]dioxol-5-yl)cyclopropanecarboxamido)-3-methylpyridin-2-yl)-t-butylbenzoate is NMT 0.8% (AUC). The solid is collected by filtration, washed with water (2×3 vol), and partially dried on the filter under vacuum. The solid is dried to constant weight (<1% difference) in a vacuum oven at 60° C. with a slight $N_2$ bleed to afford Compound 1 in Form I as an off-white solid.

An X-ray diffraction pattern calculated from a single crystal structure of Compound 1 in Form I is shown in FIG. 1. Table 1 lists the calculated peaks for FIG. 1.

TABLE 1

| Peak Rank | 2θ Angle [degrees] | Relative Intensity [%] |
|---|---|---|
| 11 | 14.41 | 48.2 |
| 8 | 14.64 | 58.8 |
| 1 | 15.23 | 100.0 |
| 2 | 16.11 | 94.7 |
| 3 | 17.67 | 81.9 |
| 7 | 19.32 | 61.3 |
| 4 | 21.67 | 76.5 |
| 5 | 23.40 | 68.7 |
| 9 | 23.99 | 50.8 |
| 6 | 26.10 | 67.4 |
| 10 | 28.54 | 50.1 |

An actual X-ray powder diffraction pattern of Compound 1 in Form I is shown in FIG. 2. Table 2 lists the actual peaks for FIG. 2.

TABLE 2

| Peak Rank | 2θ Angle [degrees] | Relative Intensity [%] |
|---|---|---|
| 7 | 7.83 | 37.7 |
| 3 | 14.51 | 74.9 |
| 4 | 14.78 | 73.5 |
| 1 | 15.39 | 100.0 |
| 2 | 16.26 | 75.6 |
| 6 | 16.62 | 42.6 |
| 5 | 17.81 | 70.9 |
| 9 | 21.59 | 36.6 |
| 10 | 23.32 | 34.8 |
| 11 | 24.93 | 26.4 |
| 8 | 25.99 | 36.9 |

Figure 3:
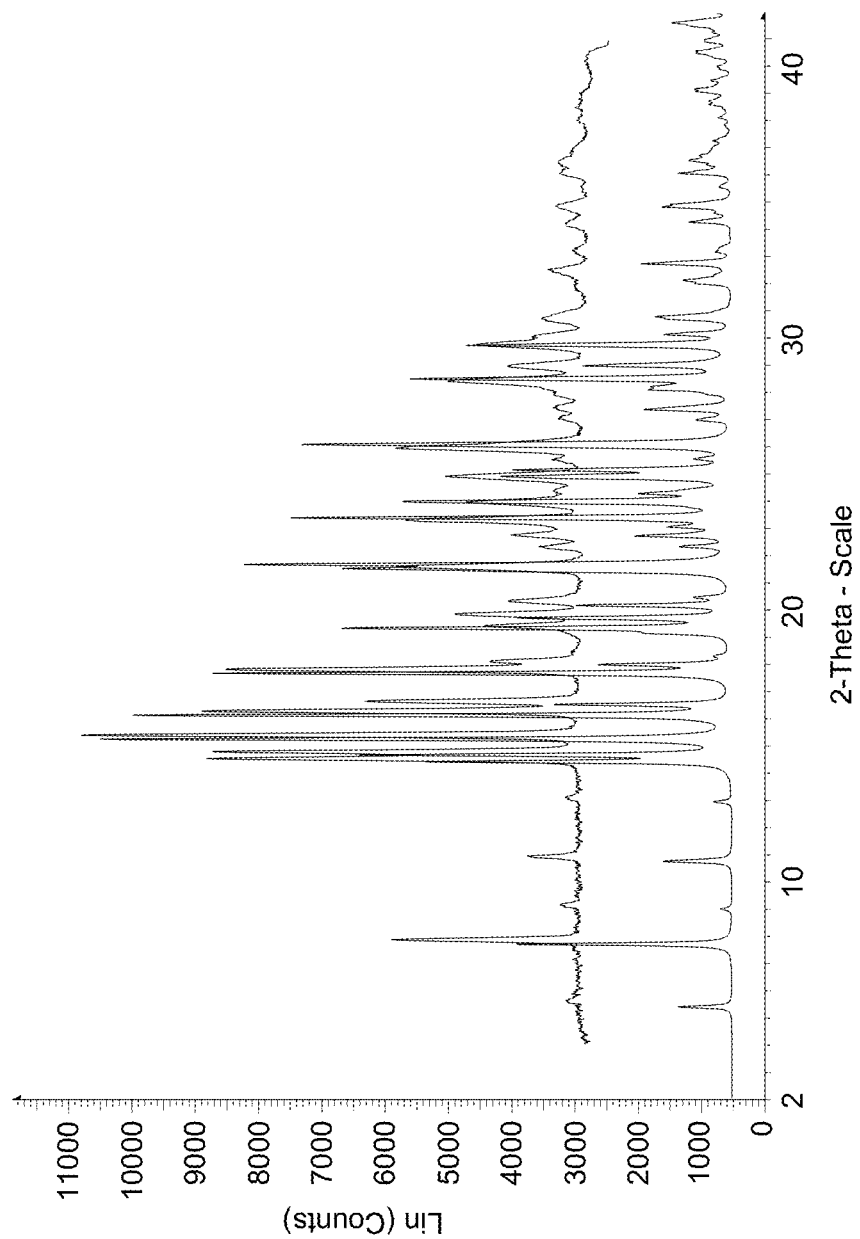
FIG. 3 is an overlay of an X-ray diffraction pattern calculated from a single crystal of Compound 1 in Form I, and an actual X-ray powder diffraction pattern of Compound 1 in Form I.

An overlay of an X-ray diffraction pattern calculated from a single crystal structure of Compound 1 in Form I, and an actual X-ray powder diffraction pattern of Compound 1 in Form I is shown in FIG. 3. The overlay shows good agreement between the calculated and actual peak positions, the difference being only about 0.15 degrees.

Figure 4:
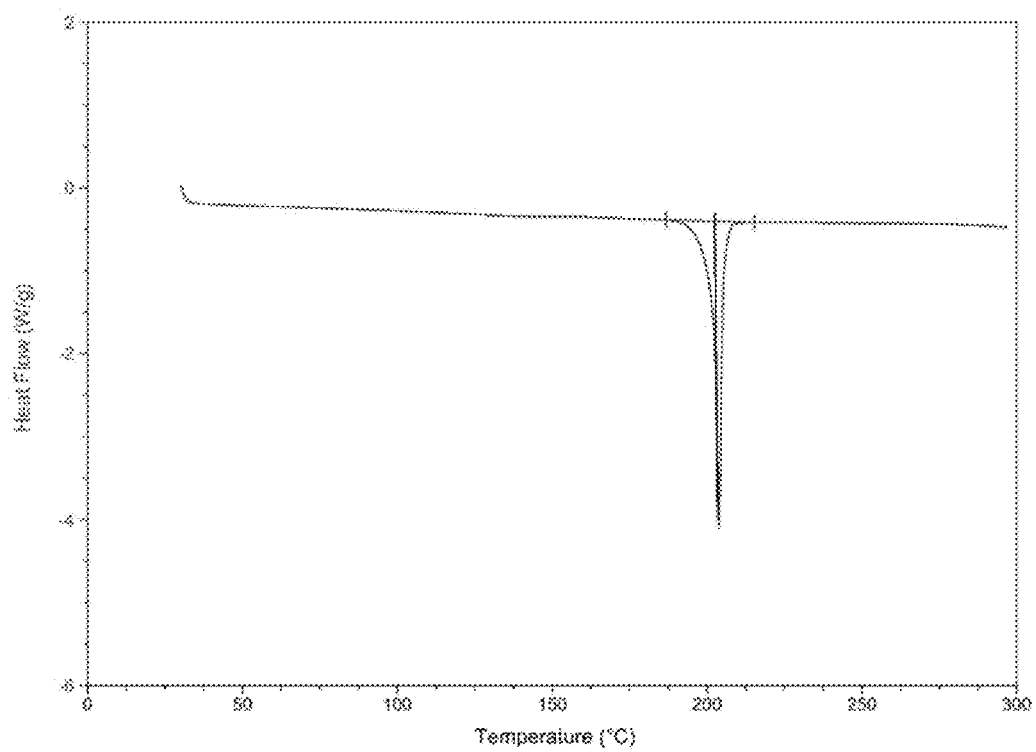
FIG. 4 is a differential scanning calorimetry (DSC) trace of Compound 1 in Form I.
Figure 5:
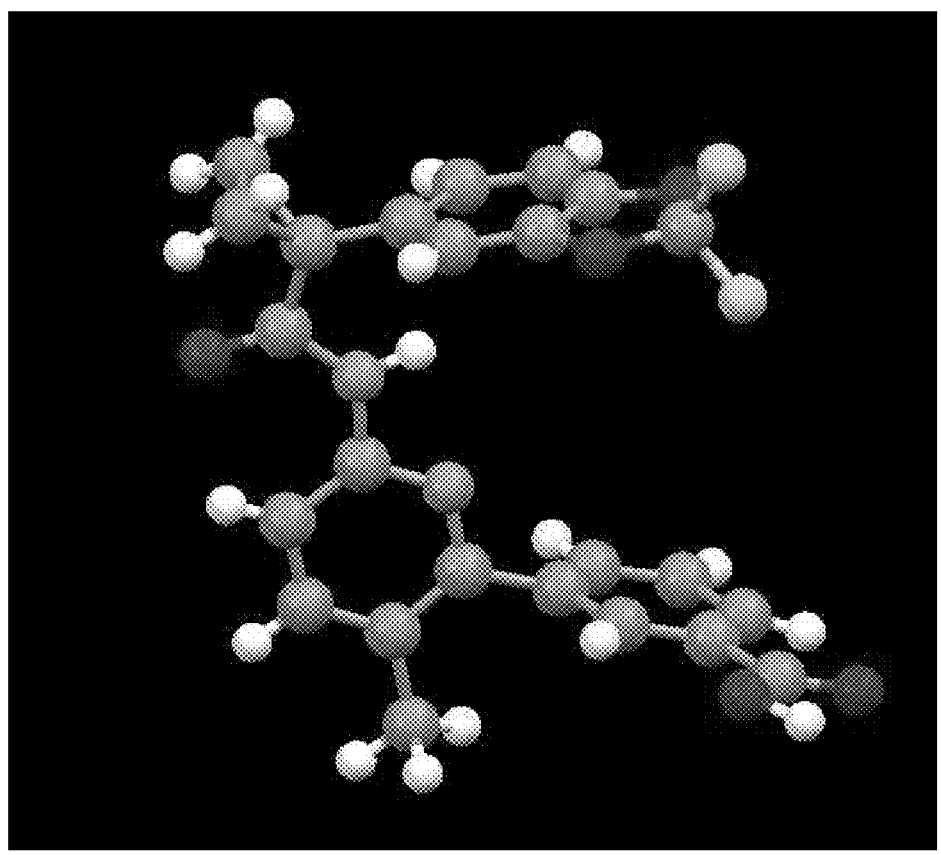
FIG. 5 is a conformational picture of Compound 1 in Form I based on single crystal X-ray analysis.

The DSC trace of Compound 1 in Form I is shown in FIG. 4. Melting for Compound 1 in Form I occurs at about 204° C.

Figure 6:
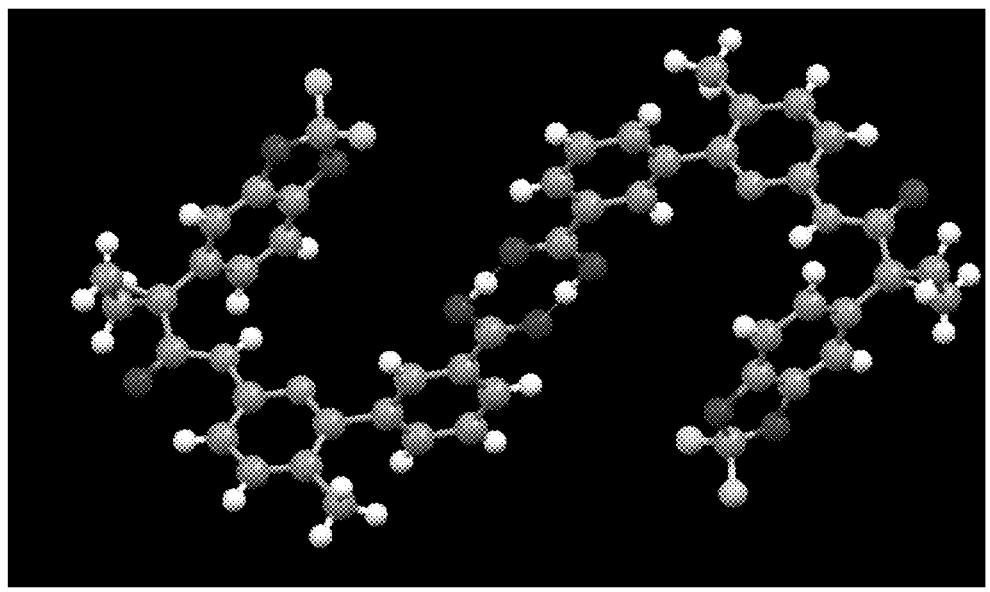
FIG. 6 is a conformational picture of Compound 1 in Form I based on single crystal X-ray analysis as a dimer formed through the carboxylic acid groups.
Figure 7:
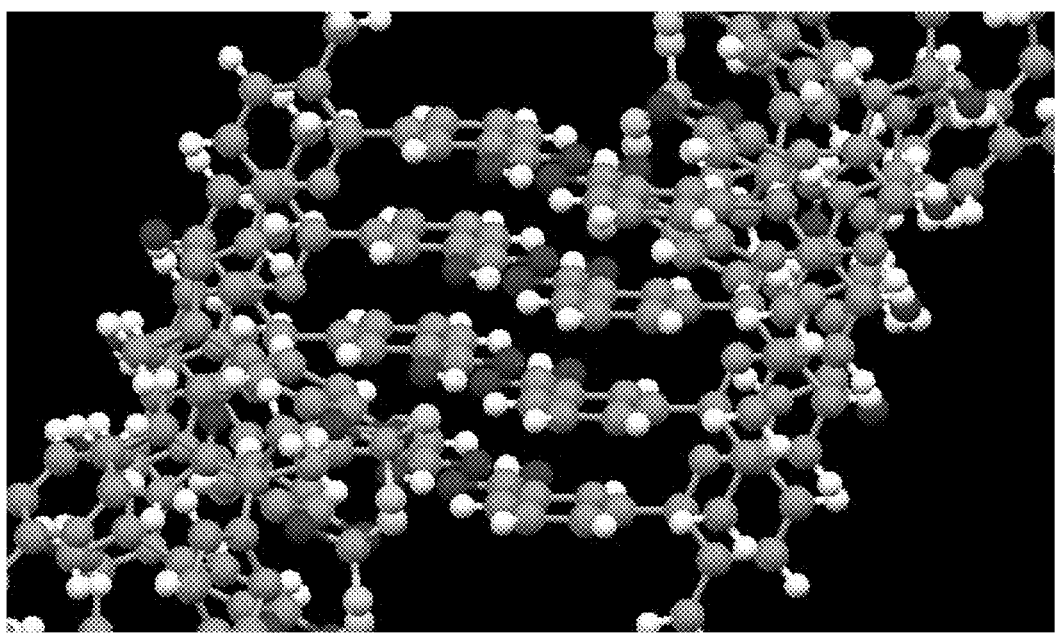
FIG. 7 is a conformational picture of Compound 1 in Form I based on single crystal X-ray analysis showing that the molecules are stacked upon each other.
Figure 8:
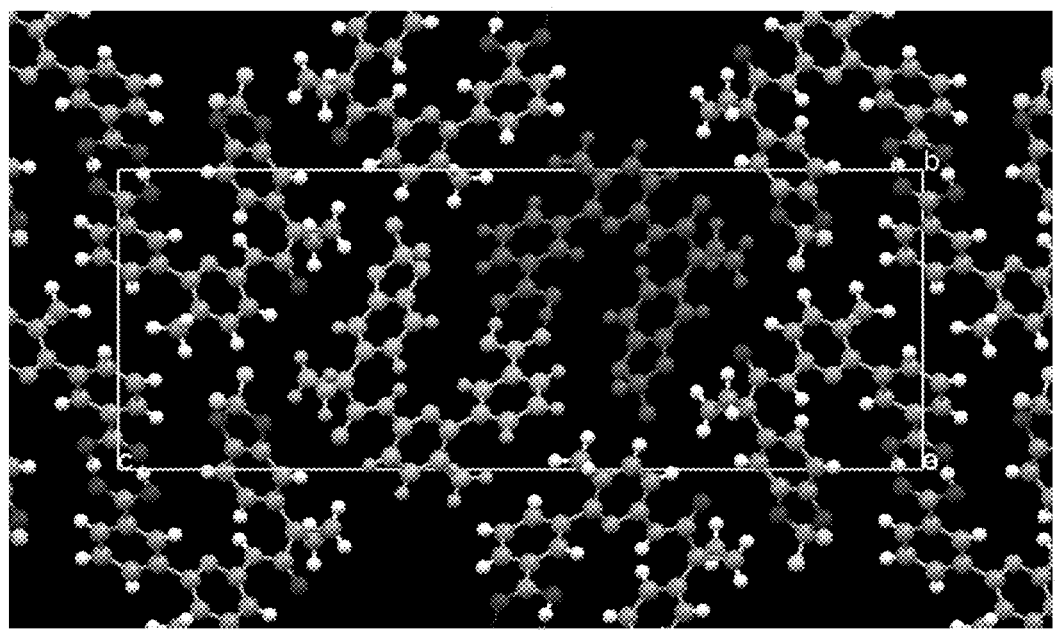
FIG. 8 is conformational picture of Compound 1 in Form I based on single crystal X-ray analysis showing a different view (down a).

Conformational pictures of Compound 1 in Form I based on single crystal X-ray analysis are shown in FIGS. 5-8. FIGS. 6-8 show hydrogen bonding between carboxylic acid groups of a dimer and the resulting stacking that occurs in the crystal. The crystal structure reveals a dense packing of the molecules. Compound 1 in Form I is monoclinic, $P2_1/n$, with the following unit cell dimensions: a=4.9626(7) Å, b=12.299 (2) Å, c=33.075 (4) Å, $\beta$=93.938(9)°, V=2014.0 Å$^3$, Z=4. Density of Compound 1 in Form I calculated from structural data is 1.492 g/cm$^3$ at 100 K.

Figure 9:
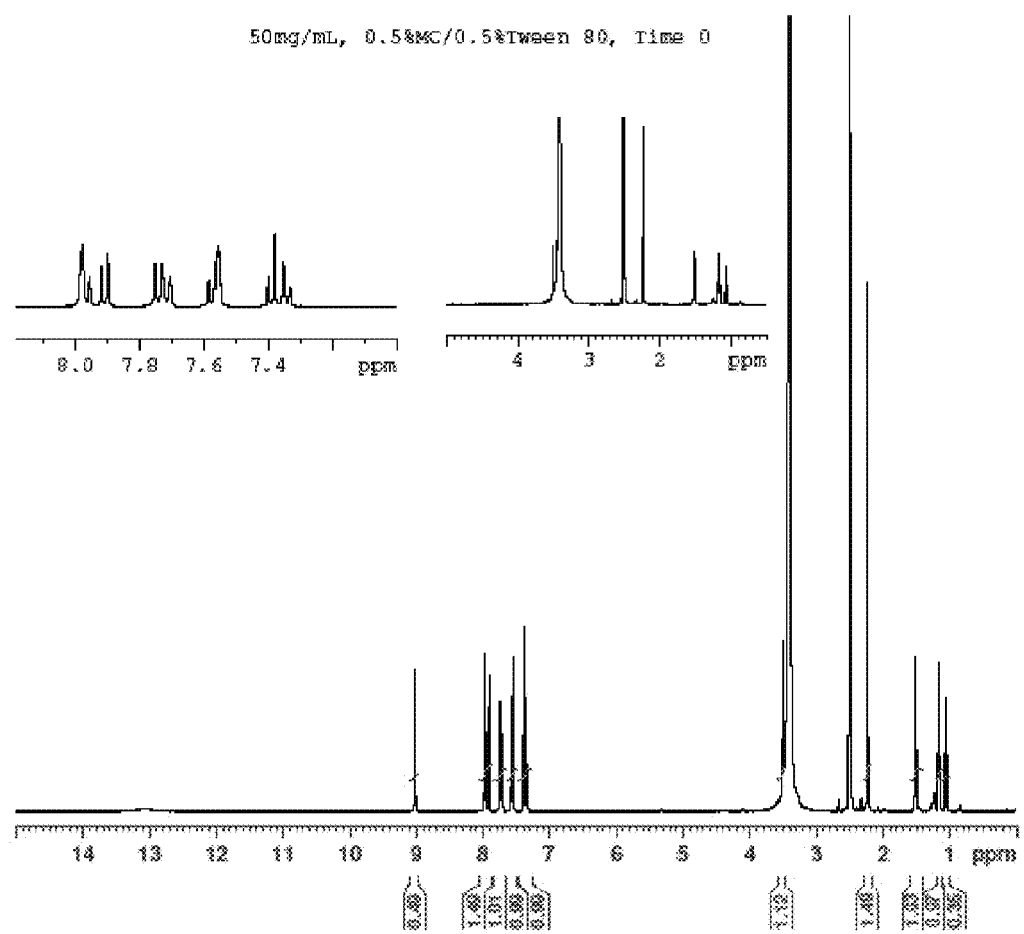
FIG. 9 is an $^1$HNMR analysis of Compound 1 in Form I in a 50 mg/mL, 0.5 methyl cellulose-polysorbate 80 suspension at T(0).
Figure 10:
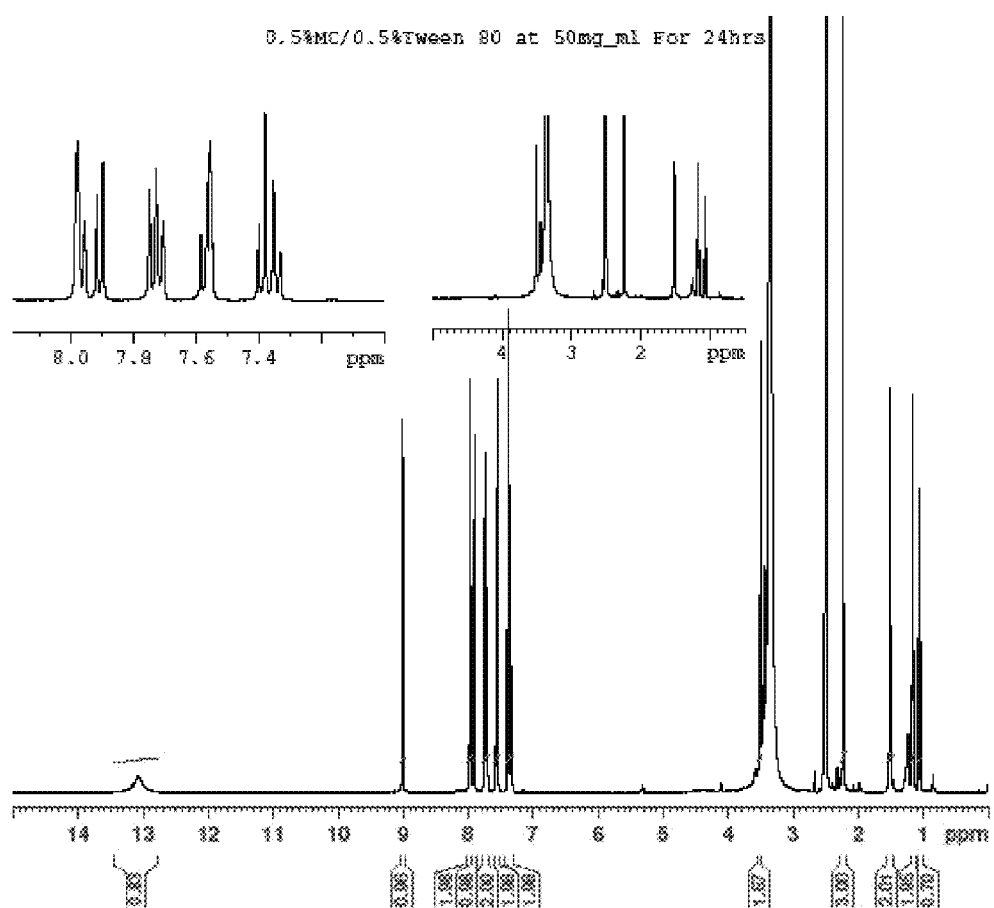
FIG. 10 is an $^1$HNMR analysis of Compound 1 in Form I in a 50 mg/mL, 0.5 methyl cellulose-polysorbate 80 suspension stored at room temperature for 24 hours.
Figure 11:
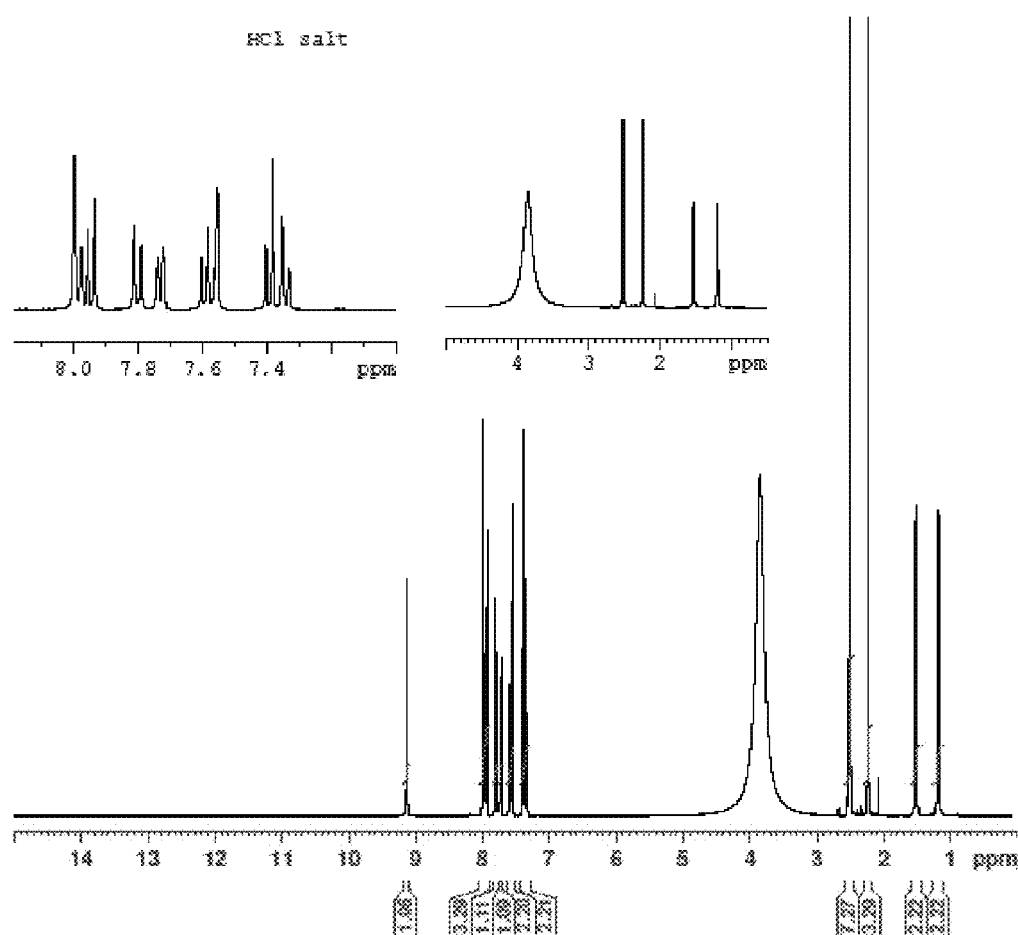
FIG. 11 is an $^1$HNMR analysis of Compound 1.HCl standard.

$^1$HNMR spectra of Compound 1 are shown in FIGS. 9-11 (FIGS. 9 and 10 depict Compound 1 in Form I in a 50 mg/mL, 0.5 methyl cellulose-polysorbate 80 suspension, and FIG. 11 depicts Compound 1 as an HCl salt).

Table 3 below recites additional analytical data for Compound 1.

TABLE 3

| Cmpd. No. | LC/MS M + 1 | LC/RT min | NMR |
|---|---|---|---|
| 1 | 453.3 | 1.93 | H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H) |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with CL-free medium to each well. The addition of CL-free medium promoted Cl$^-$ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a CL-free medium with or without test compound was added to each well. After 22 sec, a second addition of Cl$^-$-free medium containing 2-10 μM forskolin was added to activate ΔF508-CFTR. The extracellular Cl$^-$ concentration following both additions was 28 mM, which promoted Cl$^-$ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Using Chamber Assay Using chamber experiments were performed on polarized epithelial cells expressing ΔF508-CFTR to further characterize the ΔF508-CFTR modulators identified in the optical assays. FRT$^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^-$ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{sc}$ in compound-treated cells was normalized to the 27° C. and 37° C. controls and expressed as percentage activity. Preincubation of the cells with the correction compound significantly increased the cAMP- and genistein-mediated $I_{sc}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 μg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel actdivities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions
   Extracellular solution (in mM): NMDG (150), aspartic acid (150), $CaCl_2$ (5), $MgCl_2$ (2), and HEPES (10) (pH adjusted to 7.35 with Tris base).
   Intracellular solution (in mM): NMDG-Cl (150), $MgCl_2$ (2), EGTA (5), TES (10), and Tris base (14) (pH adjusted to 7.35 with HCl).

13. Cell Culture
   NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 4.

TABLE 4

| IC50/EC50 Bins: +++ <= 2.0 < ++ <= 5.0 < + | | |
|---|---|---|
| PercentActivity Bins: + <= 25.0 < ++ <= 100.0 < +++ | | |
| Cmpd. No. | BinnedEC50 | BinnedMaxEfficacy |
| 1 | +++ | +++ |

We claim:

1. A method of treating cystic fibrosis in a mammal comprising administering to the mammal an effective amount of 3-(6-(1-(2,2-difluorobenzo[d][1,3]dioxol-5-yl)cyclopropanecarboxamido)-3-methylpyridin-2-yl)benzoic acid characterized as Form I, wherein the mammal has a defective gene that causes a deletion of phenylalanine at position 508 of the cystic fibrosis transmembrane conductance regulator amino acid sequence.

2. The method of claim 1, wherein the mammal has two copies of the defective gene.

3. The method of claim 1, wherein the Form I is characterized by one or more peaks at 15.2 to 15.6 degrees, 16.1 to 16.5 degrees, and 14.3 to 14.7 degrees in an X-ray powder diffraction obtained using Cu K alpha radiation.

4. The method of claim 3, wherein the Form I is characterized by one or more peaks at 15.4, 16.3, and 14.5 degrees.

5. The method of claim 3, wherein the Form I is further characterized by a peak at 14.6 to 15.0 degrees.

6. The method of claim 5, wherein the Form I is further characterized by a peak at 14.8 degrees.

7. The method of claim 5, wherein the Form I is further characterized by a peak at 17.6 to 18.0 degrees.

8. The method of claim 7, wherein the Form I is further characterized by a peak at 17.8 degrees.

9. The method of claim 7, wherein the Form I is further characterized by a peak at 16.4 to 16.8 degrees.

10. The method of claim 9, wherein the Form I is further characterized by a peak at 16.4 to 16.8 degrees.

11. The method of claim 10, wherein the Form I is further characterized by a peak at 16.6 degrees.

12. The method of claim 10, wherein the Form I is further characterized by a peak at 7.6 to 8.0 degrees.

13. The method of claim 12, wherein the Form I is further characterized by a peak at 7.8 degrees.

14. The method of claim 12, wherein the Form I is further characterized by a peak at 25.8 to 26.2 degrees.

15. The method of claim 14, wherein the Form I is further characterized by a peak at 26.0 degrees.

16. The method of claim 14, wherein the Form I is further characterized by a peak at 21.4 to 21.8 degrees.

17. The method of claim 16, wherein the Form I is further characterized by a peak at 21.6 degrees.

18. The method of claim 16, wherein the Form I is further characterized by a peak at 23.1 to 23.5 degrees.

19. The method of claim 18, wherein the Form I is further characterized by a peak at 23.3 degrees.

20. The method of claim 1, wherein the Form I is characterized by a diffraction pattern substantially similar to that of FIG. 1.

21. The method of claim 1, wherein the Form I is characterized by a diffraction pattern substantially similar to that of FIG. 2.

22. The method of claim 1, wherein the particle size distribution of D90 is about 82 μm or less.

23. The method of claim 1, wherein the particle size distribution of D50 is about 30 μm or less.

* * * * *

UNITED STATES PATENT AND TRADEMARK OFFICE
CERTIFICATE OF CORRECTION

PATENT NO. : 8,846,718 B2  Page 1 of 1
APPLICATION NO. : 13/933223
DATED : September 30, 2014
INVENTOR(S) : Ali Keshavarz-Shokri et al.

It is certified that error appears in the above-identified patent and that said Letters Patent is hereby corrected as shown below:

On the Title Page, Item (54) and in the Specification, Column 1, lines 2-5, in the Title,
"3-(6-(1-(2,2-DIFLUOROBENZO[D][1,3]DIOX1-5-YL) CYCLOPROPANECARBOXAMIDO)-3-METHYLPYRIDIN-2-YL) BENZOIC ACID"

should read

--3-(6-(1-(2,2-DIFLUOROBENZO[D][1,3]DIOXL-5-YL) CYCLOPROPANECARBOXAMIDO)-3-METHYLPYRIDIN-2-YL) BENZOIC ACID--.

Signed and Sealed this
Tenth Day of March, 2015

Michelle K. Lee
*Deputy Director of the United States Patent and Trademark Office*